US006285448B1

(12) United States Patent
Kuenstner

(10) Patent No.: US 6,285,448 B1
(45) Date of Patent: *Sep. 4, 2001

(54) CLINICAL ANALYTE DETERMINATION BY INFRARED SPECTROSCOPY

(76) Inventor: J. Todd Kuenstner, 26 Wild Duck Rd., Wyckoff, NJ (US) 07481

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/965,071

(22) Filed: Nov. 5, 1997

Related U.S. Application Data

(60) Provisional application No. 60/046,991, filed on May 5, 1997.

(51) Int. Cl.$^7$ .................................................. G01N 33/48
(52) U.S. Cl. .............................................................. 356/39
(58) Field of Search .................................. 356/39, 40, 41

(56) References Cited

U.S. PATENT DOCUMENTS

| | | | |
|---|---|---|---|
| 4,878,021 | 10/1989 | Granot | 324/309 |
| 4,915,111 | 4/1990 | Sano et al. | 128/653 |
| 4,997,769 | 3/1991 | Lundsgaard | 436/66 |
| 5,072,732 | 12/1991 | Rapoport et al. | 128/653.2 |
| 5,127,406 | 7/1992 | Yamaguchi | 128/633 |
| 5,137,023 | 8/1992 | Mendelson et al. | 128/633 |
| 5,178,142 | 1/1993 | Harjunmaa et al. | 128/633 |
| 5,183,042 | 2/1993 | Harjunmaa et al. | 128/633 |
| 5,204,532 | 4/1993 | Rosenthal | 250/341 |
| 5,261,405 | 11/1993 | Fossel | 128/653.2 |
| 5,337,745 | 8/1994 | Benaron | 128/633 |
| 5,377,674 | 1/1995 | Kuestner | 128/633 |
| 5,448,349 | * 9/1995 | Kasaka | 356/39 |
| 5,533,509 | 7/1996 | Koashi et al. | 128/633 |
| 5,553,616 | * 9/1996 | Ham et al. | 356/301 |

OTHER PUBLICATIONS

"Rapid Measurement of Analytes in Whole Blood with NIR Transmittance," *Leaping Ahead with Near Infrared Spectroscopy*, edited by G.D. Batten, et. al., NIR Spectroscopy Group, Royal Australian Chemical Institute, Victoria, Australia), pp. 431–436, Apr. 1994.

"Spectrophotometry of Human Hemoglobin in the Near Infrared Region from 1000 to 2500 nm," *Journal of Near Infrared Spectroscopy*, 2, 59–65, 1994.

"Noninvasive Glucose Monitoring in Diabetic Patients: A Preliminary Evaluation," *Clinical Chemistry*, vol. 38, M. Noda, et. Al, No. 9, 1992.

(List continued on next page.)

Primary Examiner—Frank G. Font
Assistant Examiner—Zandra V. Smith
(74) Attorney, Agent, or Firm—Kilpatrick Stockton LLP

(57) ABSTRACT

The present invention comprises methods for minimally invasive and noninvasive analyte determination using infrared spectroscopy. A minimally invasive in vitro method comprises obtaining a volume of a fluid sample. A minimally invasive manner of obtaining the sample includes using a laser to form a micropore on a user's skin. The sample is placed on a plane of an optically clear window, such as by pressing the window against the micropore. Infrared light is directed through the window and the sample at an angle such that the light path is approximately vertical. The resulting spectrum is measured and subjected to multivariate analysis to determine the presence of at least one analyte. A noninvasive in vivo method comprises obtaining a spectral measurement of a sample in conjunction with the arterial pulse measurement. A difference spectrum is determined by subtracting the arterial pulse trough measurement from the peak measurement. The difference spectrum is normalized by dividing by the area of the absolute value of the derivative spectrum. The presence of at least one analyte is determined by applying multivariate analysis to the normalized spectrum.

16 Claims, 14 Drawing Sheets

OTHER PUBLICATIONS

"Pulse Oximetry: Analysis of Theory, Technology and Practice," *J. Clin. Monit.*, vol. 4, pp.290–301, 1988.

"Measurement of Hemoglobin in Unlysed Blood Using Near Infrared Spectroscopy," *Applied Spectroscopy*, 48 (4), 484, 1994.

"Solid–State Matrix Effects on Near–Infrared Spectra: Interactions of Glucose and Sucrose with Amylose, Amylopectin Cellulose, and Starch—Implications for Near–Infrared Calibrations," *Applied Spectroscopy*, vol. 50, No. 2, pp. 154–160, 1996.

"Completely Noninvasive Measurements of Human Blood Glucose In Vivo Using Near Infrared Waves," *Pathogenesis and Treatment of NIDDM and its Related Problems*, Elsevier Science, B.V., 1994.

"Near–Infrared Spectrometric Determination of Hydrogen Ion, Glucose, and Human Serum Albumin in a Simulated Biological Matrix," *Spectroscopy*, James K. Drennen, et al., vol. 6, No. 2, May 1990.

"More on Derivatives. Part I. Segments, Gaps and 'Ghosts'," *NIR News*, vol. 4, No. 6.

* cited by examiner

Tissue composite shows dynamic and static componets affecting light absorption. (Courtesy of Ohmeda)

CLINICAL ANALYTE DETERMINATION BY INFRARED SPECTROSCOPY

CROSS-REFERENCES TO RELATED APPLICATIONS

This application claims the benefit of the filing date of U.S. Provisional Application No. 60/046,991, filed May 5, 1997 and entitled "Clinical Analyte Determination by Infrared Spectroscopy."

FIELD OF THE INVENTION

The present invention relates to minimally invasive and noninvasive clinical analyte determination by infrared spectroscopy, and more particularly, to methods and apparatus for measuring glucose, hemoglobin, urea, cholesterol and other analyte concentrations using infrared spectroscopy.

BACKGROUND

The measurement of the levels of blood borne analytes, including glucose, urea, cholesterol, and/or hemoglobin in a patient is an often utilized clinical procedure. Typically a needle or some other device is used to deeply penetrate a patient's skin and draw a sample, such as blood, which is then analyzed by chemical techniques to determine the concentration of the analyte(s) of interest. The drawbacks of these procedures include the pain and apprehension experienced by the patient, the risk of infection to both the patient and any health care worker handling the sample or the sample-taking device, and the delay in feedback associated with sending the sample to a laboratory for analysis.

Noninvasive techniques have been developed in order to overcome the drawbacks of the invasive techniques. For example, as described in my U.S. Pat. No. 5,377,674, the disclosure of which is incorporated herein by reference, one such branch of noninvasive techniques involves the use of spectroscopy. Spectroscopy deals with the measurement and interpretation of light waves resulting from exposing a substance to a known light wave. The measurements can be based on the reflectance, transmission or emission of the light wave. When exposing a mixture of substances to a known light wave, each of the substances absorbs, to varying degrees, parts of the light wave. As a result of this absorption, a unique light wave is created. Thus, the unique resultant light wave can be measured and interpreted to determine the presence and concentration of substances that make-up the mixture. We have shown in prior work that spectral regions may be normalized prior to PLS analysis by dividing by the area of the absolute value of the derivative spectrum to yield analyte concentration information. (Kuenstner et al., "Rapid Measurement of Analytes in Whole Blood with NIR Transmittance," *Leaping Ahead with Near Infrared Spectroscopy*, edited by G. Batten et al., Proceedings of the 6th International Conference on Near Infrared Spectroscopy at Lorne, Australia in April 1994).

Development of noninvasive techniques utilizing spectroscopy for glucose monitoring would be particularly advantageous because of the large number of diabetics who would benefit from such a discovery. Currently, glucose testing requires taking a blood sample with the use of a steel lancet as often as 4 times a day. The sample is then analyzed using a glucose meter. The meter, however, requires the blood sample to be collected on a reagent strip. Reagent strips are not re-usable and are a significant expense for diabetics who need to frequently monitor their glucose level.

Infrared (IR) light has been used for glucose measurement in current noninvasive spectroscopic techniques. These techniques typically involve the use of an Attenuated Total Reflectance (ATR) accessory in combination with Partial Least Squares (PLS) and/or Partial Least Squares with Artificial Neural Networks (PLS-ANN) analysis to measure the resultant light wave and determine the concentration of glucose in the sample. The equipment and methods required to perform these techniques, however, are quite complicated.

A major disadvantage of these techniques is the requirement of ATR accessories. Generally, ATR accessories include a special crystal that precisely modifies the path length of the infrared light in relation to the sample. The ATR crystal directs the light to be reflected between the bottom of the sample and the crystal a number of times. This results in reflected wave measurements that change over time if a suspension like blood is used. Measurements on a suspension such as blood made with an ATR crystal change over time as a result of settling of constituents within the blood sample. For example, the concentration of red blood cells at the bottom surface of a sample of whole blood will increase over time as the red blood cells settle to the bottom of the sample. This phenomenon creates problems in the ATR measurement technique.

Also, special equipment arranged in a precise set-up is required to measure the resultant reflected light waves. The set up needs to be precise to guarantee a specific incident angle of the light. Additionally, the ATR crystal must often be thoroughly cleaned between samples in order to obtain accurate results. Thus, problems with crystal cleaning and instrument readjustment in such an exacting environment do not lend these methods to quick, easy and simple use by diabetics.

Efforts have been made to avoid some of the problems associated with the ATR accessories while maintaining at least a similar level of accuracy. For example, Budinova et al. took spectroscopic measurements on dried blood and serum samples using infrared transmission. G. Budinova, J. Salva and K. Volka, "Application of Molecular Spectroscopy in the Mid-Infrared Region for the Determination of Glucose and Cholesterol in Whole Blood and in Blood Serum," *Applied Spectroscopy*, Vol. 51(5), p. 631, 1997. Measuring the transmittance of infrared waves is less complex than the ATR measurements, but there are some drawbacks. For example, dried samples were required because of the difficulty in obtaining accurate results with liquid blood or serum. Budinova et al. found that "transmittance measurements of liquid blood or serum are impossible in the mid-IR because of the presence of water in the matrix." Id. They disclose a method requiring careful pipetting of a fixed volume of sample onto a polyethylene carrier, and then drying the sample prior to spectroscopic analysis. Additionally, they normalized the resultant spectrum by multiplying by the ratio of the chosen area of 100 to the integrated spectrum area. In essence, this approach is based on the assumption that the total concentration of the main blood or serum components is roughly constant.

Other transmittance, reflectance and emission techniques have been developed for measuring analytes in samples. In general, however, these methods have been found to be accurate for some, but not all, patients. To improve the accuracy, the prior art typically requires the use of complex analysis, complex equipment, or both. Thus, these methods are not well-suited for convenient, quick and simple use.

Additionally, to overcome the delay in feedback associated with sending the sample to a laboratory for analysis, the use of point of care testing has increased. Generally, this type of testing means that patient samples are tested at the bedside or within the intensive care unit of the hospital ward rather than in a centralized laboratory. Many of the present point of care methods, however, are more expensive than the conventional methods. For example, one widely-used point of care device, made by I-Stat Corporation, analyzes whole blood for sodium, potassium, chloride, $CO_2$, urea, glucose and hematocrit. The cost of reagents for this panel of tests is about twelve dollars. In contrast, the reagent cost per analyte for a typical large central laboratory analyzer is on the order of a few cents. Thus, the benefit and practicality of current devices providing immediate feedback may be outweighed by the cost, especially given the fiscal constraints of today's hospital environment.

SUMMARY OF THE INVENTION

The present invention advantageously provides apparatus and methods for measuring analytes which overcomes the disadvantages of the heretofore utilized methods discussed above. Aspects of the present invention include a device and method for minimally invasive in vitro and non-invasive in vivo measurements of analytes that are accurate and easily used.

In an embodiment of the present invention, a substantially optically clear window is placed in contact with a micropore in the skin to collect a fluid sample. In a preferred embodiment the micropore is a bloodless micropore comprising interstitial fluid which may be painlessly formed utilizing a laser. The fluid sample is covered by another window and inserted into a holder that situates the sample for a spectrophotometric analysis. The resulting spectrum is analyzed to determine an analyte concentration. This aspect of the present invention may be advantageously utilized to determine the concentration of analytes such as glucose, cholesterol and urea. If the sample obtained comprises whole blood, hemoglobin concentration may be determined. This embodiment of the present invention provides a device and method that can easily and advantageously be used, for example, by diabetics for home care or by health care workers in a point of care setting.

In the methods and apparatus of the present invention spectral information is preferably obtained over the spectral areas where an analyte or analytes of interest exhibit increased absorption (high molar absorptivity) in comparison to other substances in the same spectral region.

In preferred embodiments of the present invention, the spectrophotometric analysis comprises obtaining a vertical transmittance measurement of mid-infrared light. A vertical transmittance measurement eliminates changes in spectra due to settling of suspended particles in the fluid sample. An accurate measurement of analyte concentration may be obtained with the present invention without strict controls over sample volume or light path length, however, as described in detail below, some control of light path length may yield improved results.

Also, the present invention is cost efficient and flexible through the capability to utilize both reusable and disposable windows. An embodiment of a device of the present invention may utilize substantially permanent windows, comprising transparent media in the infrared region, such as barium fluoride, which may be cleaned and reused. This embodiment may be utilized in the home care setting wherein a user simply washes off and dries the reusable windows in order to prepare them for reuse. This reduces the per measurement cost of the system compared to current devices, as new strips of expensive reagents are not required.

Another embodiment of a device of the present invention may utilize disposable windows, comprising, for example, thin films of polyethylene. In this embodiment, the windows would be changed after a single use of the device. In a hospital or clinic setting, disposable windows may be utilized to eliminate any risk of infection from patient to patient and/or patient to health care provider.

Another aspect of the present invention provides a noninvasive means to determine the concentration of blood borne analytes. The noninvasive in vivo embodiment comprises obtaining a spectral measurement of a sample in conjunction with the arterial pulse. A difference spectrum is determined by subtracting the arterial pulse trough from the peak measurement. The difference measurement is normalized by dividing by the area of the absolute value of the derivative spectrum. The derivative spectrum may comprise first, second, third or other order derivative spectrum. Use of the second derivative spectrum may be preferred in certain embodiments of the present invention. The presence of at least one analyte is determined by applying multivariate calibration analysis to the normalized spectrum.

The present invention may be used to determine the presence of analytes such as glucose, hemoglobin, urea and cholesterol, among others.

It is therefore an advantage of the present invention to provide a simple device and method for clinical analyte determination using infrared spectroscopy.

Another advantage is that the present invention provides a cost-effective point of care method and device for analyte determination.

A further advantage of the present invention is the versatility of a system which utilizes re-usable or disposable cells.

Moreover, the device and methods of the present invention offer the benefit of considerable cost savings to the patient and their insurors. Currently marketed glucose level monitoring devices for home use require the use of disposables. Over time, for example a patient's life, the cost of the disposables is considerable. In today's market, a typical cost for test strips may be up to $65.00 per 100 strips. Assuming the strips are used at a rate of 4 per day, the annual cost of the strips is approximately $949.00. For a juvenile diabetic who has the disease for a lifetime of 50 years, the total cost would be approximately $47,450.00.

DETAILED DESCRIPTION OF THE INVENTION

The present invention comprises methods for minimally invasive and noninvasive analyte determination using infrared spectroscopy. A minimally invasive in vitro method comprises obtaining a volume of a fluid sample and contacting the sample on a plane of an optically clear window. A second window is placed against the sample and the first window thereby creating a sandwich of liquid film between the windows. Infrared light is directed through the window and the sample at an angle approximately perpendicular to the plane of the window. The resulting spectrum is measured and analyzed to determine the presence of at least one analyte.

Figure 1:
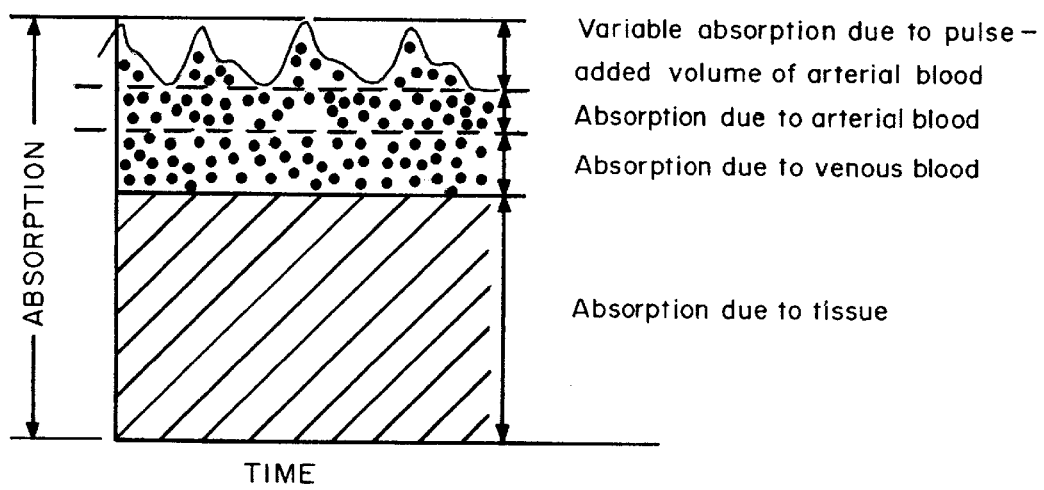
FIG. 1 is a diagram depicting the dynamic and static components affecting light absorption in tissue taken from M. W. Wukitsch, M. T. Petterson, D. R. Tobler, and J. A. Pologe, "Pulse Oximetry: Analysis of Theory, Technology and Practice," *J. Clin. Monit.*, Vol. 4, pp. 290–301, 1988.

A noninvasive in vivo method comprises obtaining a spectral measurement of a sample in conjunction with the arterial pulse. A difference spectrum is determined by subtracting the arterial pulse trough measurement from the peak measurement. An example of a difference spectrum is illustrated in FIG. 1. The difference measurement is normalized by dividing by the area of the absolute value of the derivative spectrum. The presence of at least one analyte is determined by applying multivariate calibration analysis to the normalized spectrum.

Figure 2:
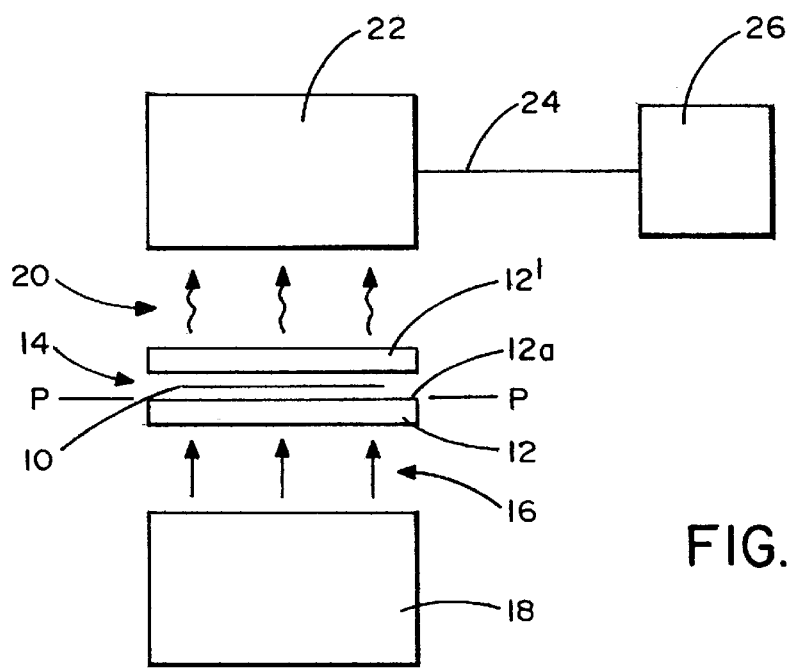
FIG. 2 is a schematic representation of the set-up of the present invention.
Figure 3:
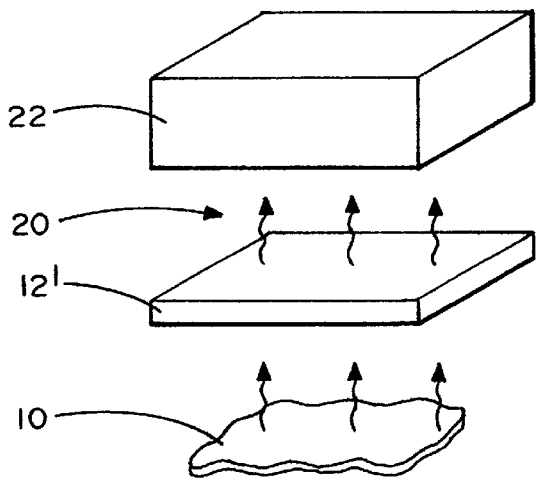
FIG. 3 is a partial exploded view of the set-up of the present invention.
Figure 3:
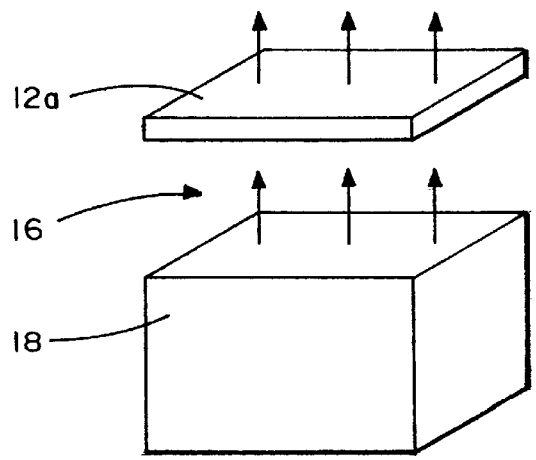

Referring to FIGS. 2 and 3, the preferred system of minimally invasive analyte determination comprises contacting a fluid sample 10 with an optically clear window 12. Fluid sample 10 is a bodily fluid, such as blood, but preferably is interstitial fluid. In order to obtain sample 10, a minimally invasive technique is utilized on a patient. A device (not shown), such as one made by SpectRx of Norcross, Ga., may be used. The SpectRx device utilizes a laser to create a tiny, shallow ulcer, or micropore, on a patient's skin which fills with interstitial fluid in about 15 seconds. The depth of the micropore is controlled to avoid affecting nerves and capillaries in the deeper layers of the skin. Thus, the micropore is painless and bloodless.

Sample 10 is disposed, through direct contact and capillary action, on a side 12a of window 12. Side 12a lies in plane p—p in FIG. 2, which represents a horizontal plane. Disposing sample 10 on window 12 may be advantageously accomplished, for example, by a diabetic patient pressing window 12 against a micropore in their skin. In contrast to prior art teachings, no control or measurement of the volume of sample 10 is required in the present invention. Another window 12' may be apposed on top of sample 10, although this is not necessary. Opposing window 12' against sample 10 helps to prevent evaporation of the sample, which beneficially leads to more stable measurements over time.

The use of windows 12 and 12' creates stack 14 (see FIG. 2) comprising a thin layer of sample 10 disposed between windows 12 and 12'. The use of mid-infrared spectroscopy on thin films of liquid sandwiched between optical windows for the purpose of quantitative analysis is not generally done in spectroscopy. Generally, spectroscopic measurements of a thin layer of liquid are limited to obtaining the spectrum of the pure sample without regard to quantitative analysis of analyte concentrations, as provided by the present invention.

Windows 12 and 12' preferably comprise a substantially optically clear material that minimizes the distortion and absorption of light waves. Materials should be selected such that their distortion or absorption of light waves, if any, is at a part of the spectrum away from the absorption of light waves in the analyte to be studied. Examples of such materials are barium fluoride and polyethylene, but those skilled in the art will recognize that other similar materials may be used. The absorption bands of various analytes are discussed below. Distorting materials can be used, however, with the drawbacks of adding extra steps to the analysis and giving less accurate results. The extra steps are required to independently measure the spectrum of the window and subtract it out of measurements of the sample. The less accurate results are due to the interference between the absorption of light waves between the sample and the windows.

The present invention advantageously allows the use of optically clear materials suitable for re-use, such as barium fluoride, or a material suitable for one-time disposable use, such as polyethylene. This versatility makes the present invention attractive to both clinical and home use. The disposable windows may be preferred by the clinical users in order to reduce the risk of transmitting infections. Meanwhile, a home user may prepare the windows for re-use by simply cleaning them with water and drying them off.

Stack 14, or sample 10 disposed on window 12, are placed in the path of light waves 16 generated by source 18. Waves 16 are infrared waves, preferably from the mid-infrared range of about 1185 to 960 cm$^{-1}$. Waves 16 from the near infrared range may also be used. Use of mid-infrared waves, however, advantageously allows for smaller sample volumes.

Figure 4:
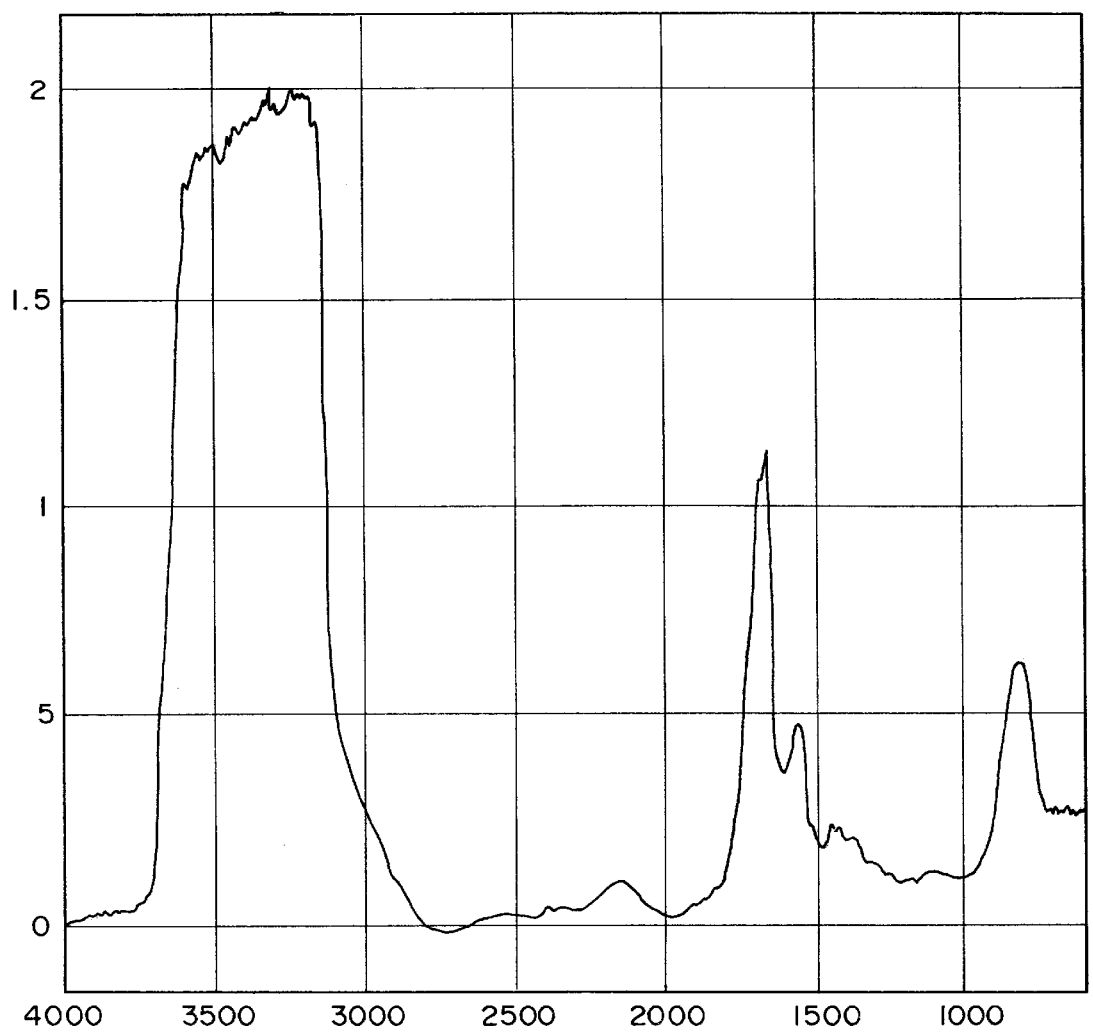
FIG. 4 is a graph of the spectrum of a whole blood sample.

Waves 16 are directed through window 12 and transmitted through sample 10, which alters waves 16 and creates resultant spectrum 20. FIG. 4 is a representative spectrum of whole blood. Resultant spectrum 20 may then pass through window 12' and onto detector 22, which measures the spectrum. Since windows 12 and 12' comprise a substantially optically clear material, resultant spectrum 20 is a function of sample 10. Detector 22 sends a signal 24, representing spectrum 20, to computer 26 which analyzes signal 24 to obtain an analyte concentration determination.

Preferably the path of light waves 16 is approximately perpendicular to window plane 14a. A vertical path of waves 16 was found to be advantageous on samples 10 of whole blood, as spectrum 20 obtained using a horizontal light path were constantly changing due to settling of red blood cells. This settling adversely affects the prior art studies on whole blood samples using the typical Attenuated Total Reflectance (ATR) set-up. In studies of plasma or serum samples 10, however, a vertical path is not as important since there is much less settling of material within the sample. Yet, the vertical path is still advantageous as lipid and protein particles, for example, may settle over time in a plasma or serum sample.

Strict control over the thickness of sample 10 (path length) is not required for accurate results. Path length may be unknown and vary between thicknesses yielding absorbances of between 0.1 and 0.8, preferably between 0.2 and 0.7, in contrast with the prior art which requires a constant, known and precisely-controlled path length. Control over path length is not essential in the present invention for a number of reasons.

It was found that spectrum 20 could be normalized for path length changes prior to analysis. This normalization involves dividing the measured spectrum 20 by the area of the absolute value of the derivative spectrum. Partial Least Squares (PLS) analysis can then be performed to determine analyte concentration. Alternatively, it was surprisingly found that the PLS analysis itself could handle the changing path lengths without normalization. Normalization is advantageous, however, because it reduces the number of factors required for PLS analysis from 15 to 8.

Figure 5:
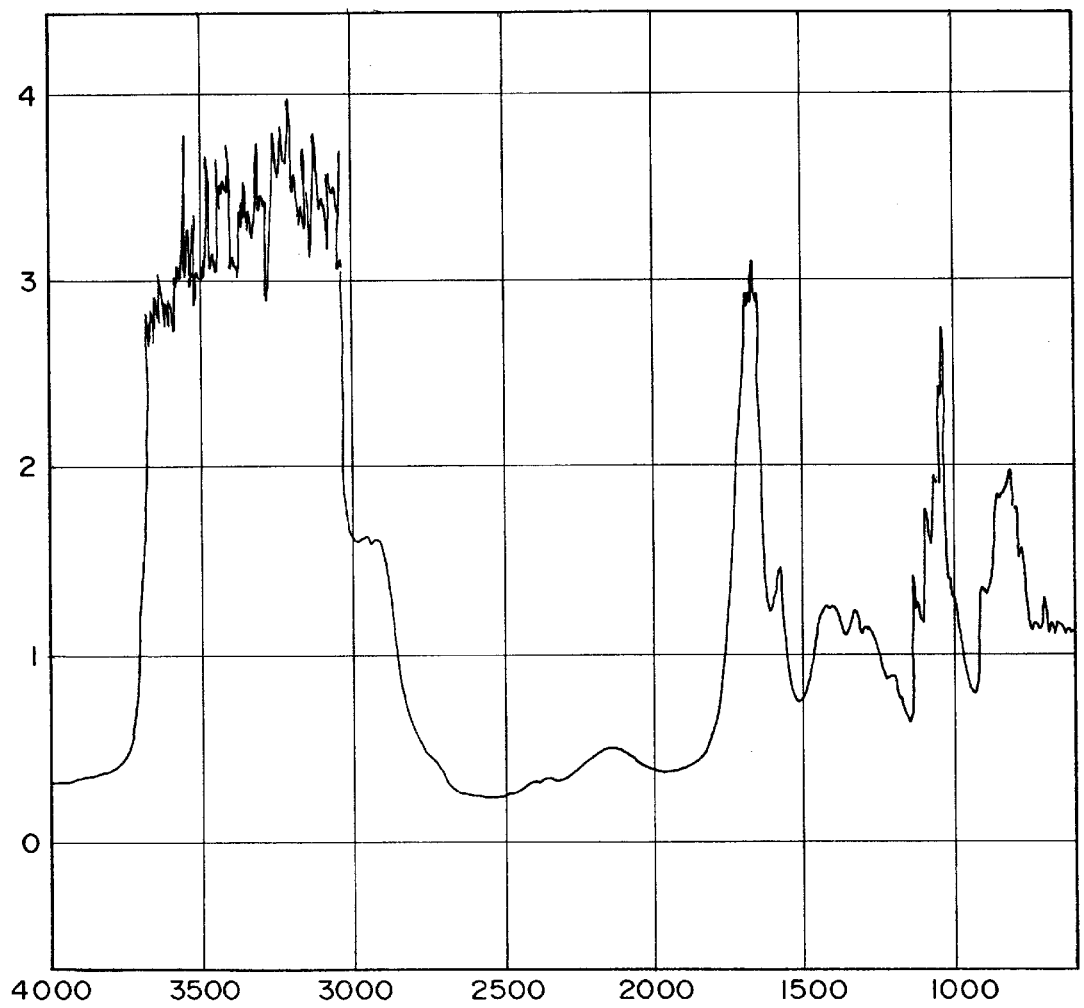
FIG. 5 is a graph of the spectrum of a whole blood sample spiked with glucose.
Figure 6:
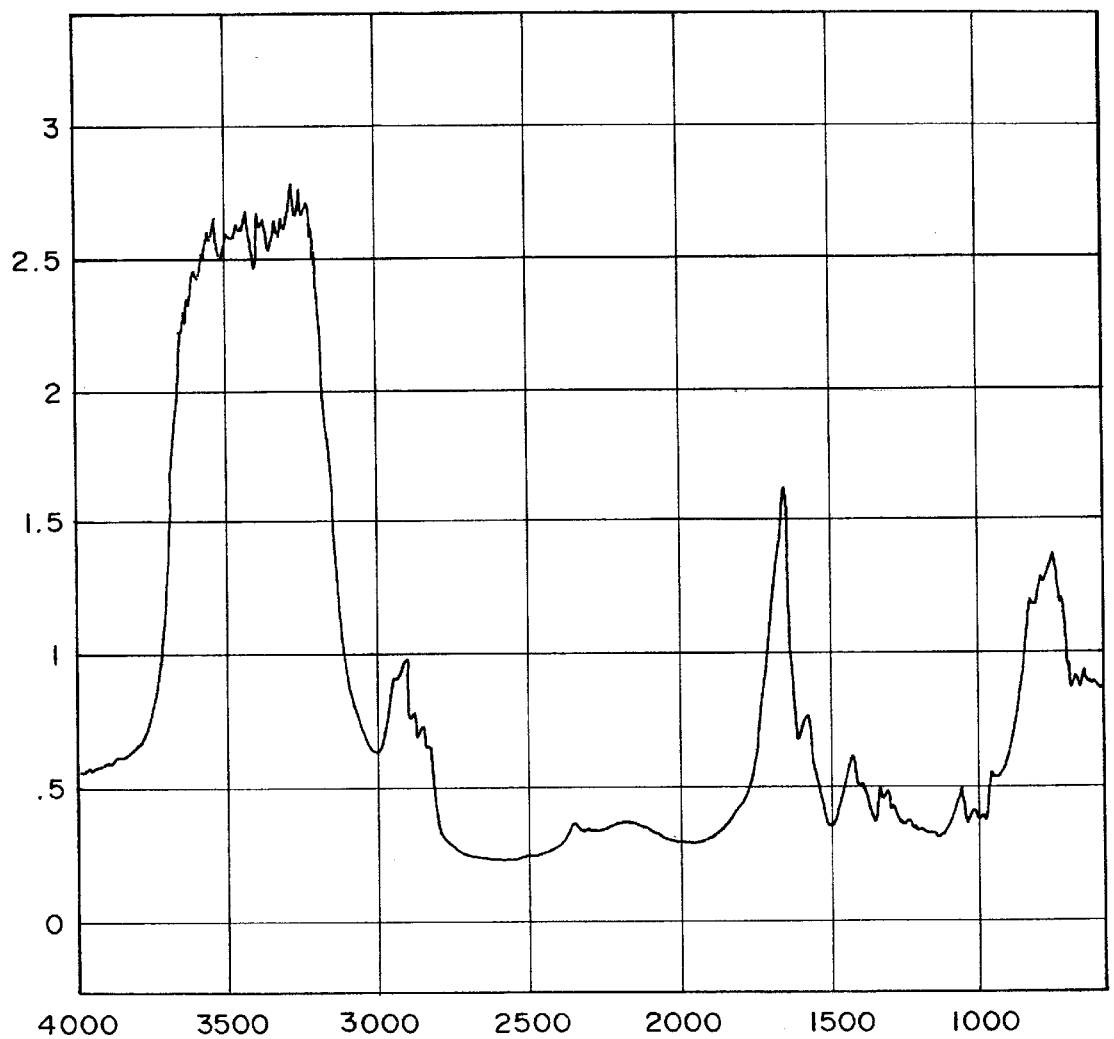
FIG. 6 is a graph of the spectrum of a whole blood sample spiked with cholesterol.
Figure 7:
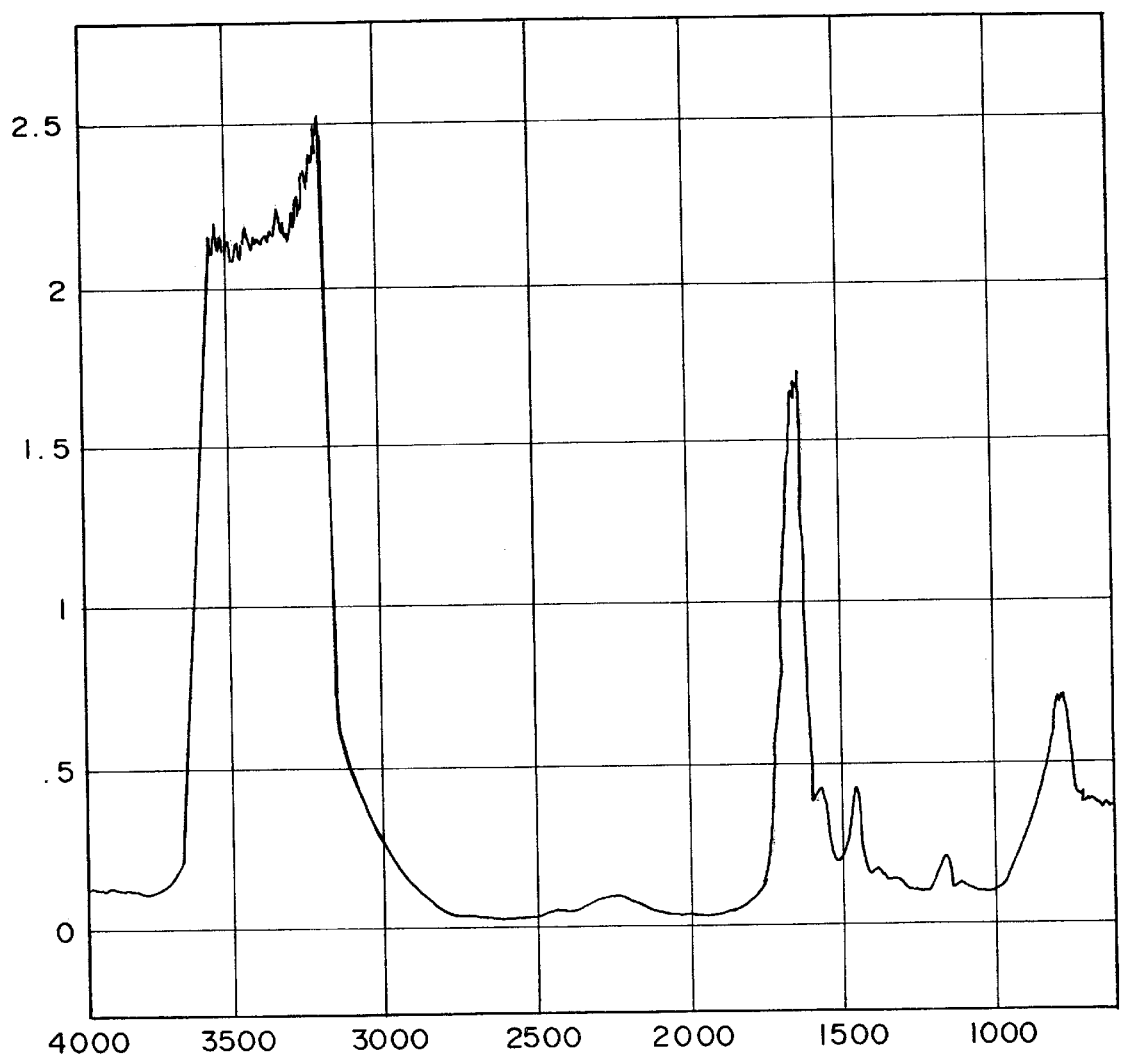
FIG. 7 is a graph of the spectrum of a whole blood sample spiked with urea.

The PLS analysis is applied only to regions of the spectrum in which the analyte has a strong absorption band that is not obscured by nearby absorption bands of water. Other regions of the spectrum can be ignored since inclusion of such regions lowers the accuracy of the measurement. For example, the PLS analysis was applied to the region of the C—O (carbon-oxygen) stretching band of glucose which occurs between about 1185 $cm^{-1}$ and 960 $cm^{-1}$. A strong absorption band can be seen in FIG. 5, which is a spectrum of whole blood spiked with glucose. Similar to glucose, the PLS analysis is applied to the range of about 1185 $cm^{-1}$ and 960 $cm^{-1}$ for hemoglobin. In the case of cholesterol, PLS analysis was applied to the region of steroid ring C—H (carbon-hydrogen) stretching found between about 3000 $cm^{-1}$ and 2800 $cm^{-1}$. A strong absorption band can be seen in FIG. 6, which is a spectrum of whole blood spiked with cholesterol. Finally, in the case of urea, PLS analysis was applied to the region of about 1500 $cm^{-1}$ to 1420 $cm^{-1}$. A strong absorption band can be seen in FIG. 7, which is a spectrum of whole blood spiked with urea. This absorption band is most likely due to interaction between the N—H (nitrogen-hydrogen) bending and the C—N (carbon-nitrogen) stretching of the C—N—H (carbon-nitrogen-hydrogen) group.

Light source 18 may comprise any device capable of generating infrared light, preferably in the mid-infrared range of about 1185 to 960 $cm^{-1}$. Preferably source 18 is specially adapted for application of clinical analyte determination as defined by the present invention. Many features of currently available sources may thus be eliminated. For example, the reagentless device of the present invention does not need a purge function to eliminate water vapor and $CO_2$. Additionally, the device would not necessarily require cooling. Also, a monochromator comprising a grating, rather than a prism, is preferred since some prism materials may be damaged by moisture.

Similar to source 18, detector 22 may be specially adapted for use with the present invention. Currently available devices capable of sensing and measuring infrared light, however, may still be used. For example, a tri-glycine sulfate detector, which advantageously does not require cooling, may be used. This type of detector, however, may not have enough sensitivity, depending on the required measurement.

Figure 8:
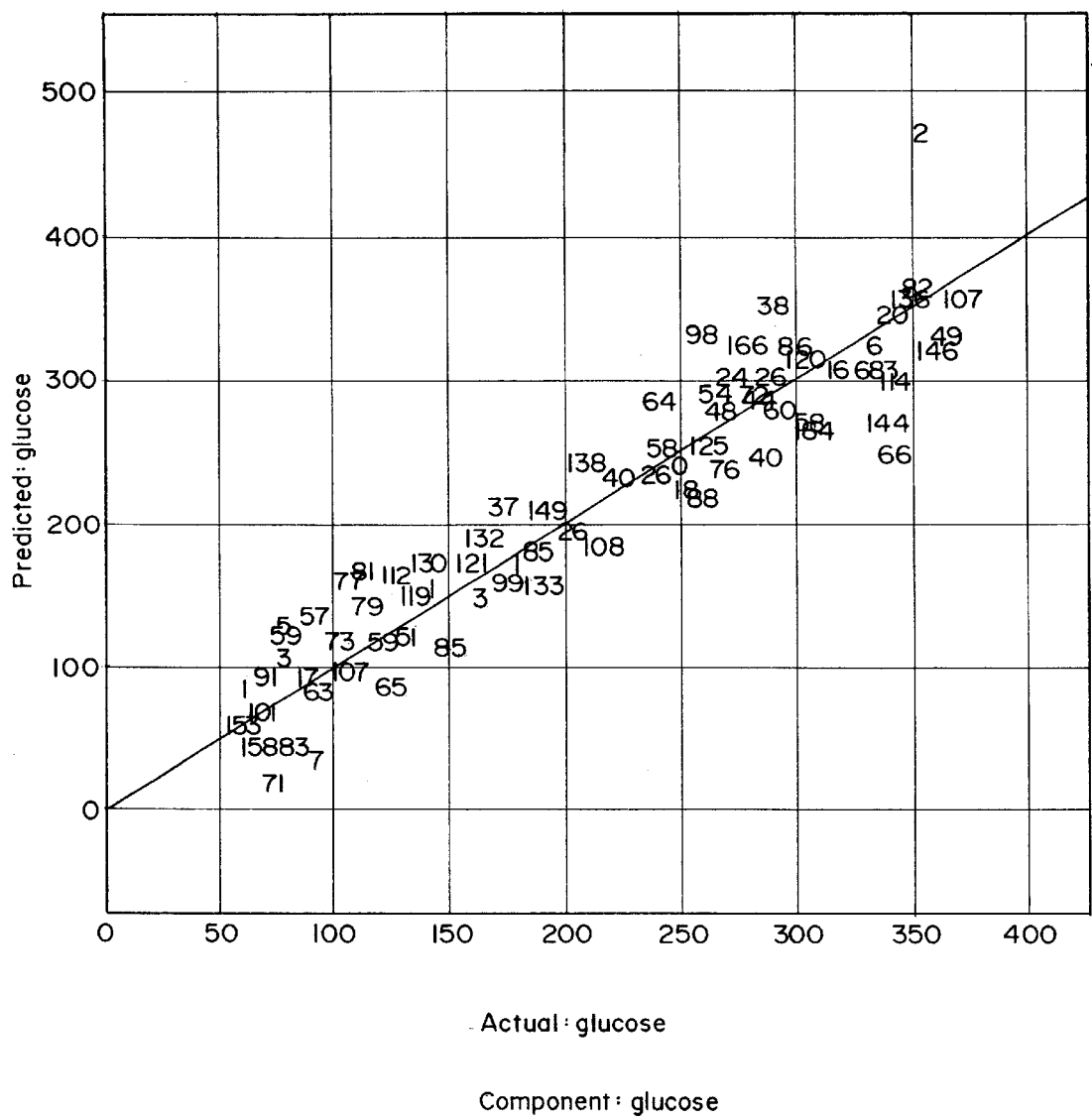
FIG. 8 is a graph of the correlation between glucose measurements made with the present invention and a calibration set of 169 whole blood samples.

FIG. 8 represents a correlation chart for spectroscopic measurements of glucose using mid-range infrared light from the region of about 1185 to 960 $cm^{-1}$ on a calibration set of 169 whole blood samples which were collected in sodium fluoride. The glucose values of this calibration set ranged from 62 to 358 mg/dL. Using the present invention and requiring 8 factors, glucose measurements resulted in an $R^2$ of 0.922 and a Root Mean Squared Deviation (RMSD) of 23.4 mg/dL compared to the reference method. On an independent validation set of 37 whole blood samples with a range of glucose concentration from about 67 to 338 mg/dL, an $R^2$ of 0.94 and a Standard Error of Prediction (SEP) of 24.8 mg/dL using the calibration equation.

Figure 9:
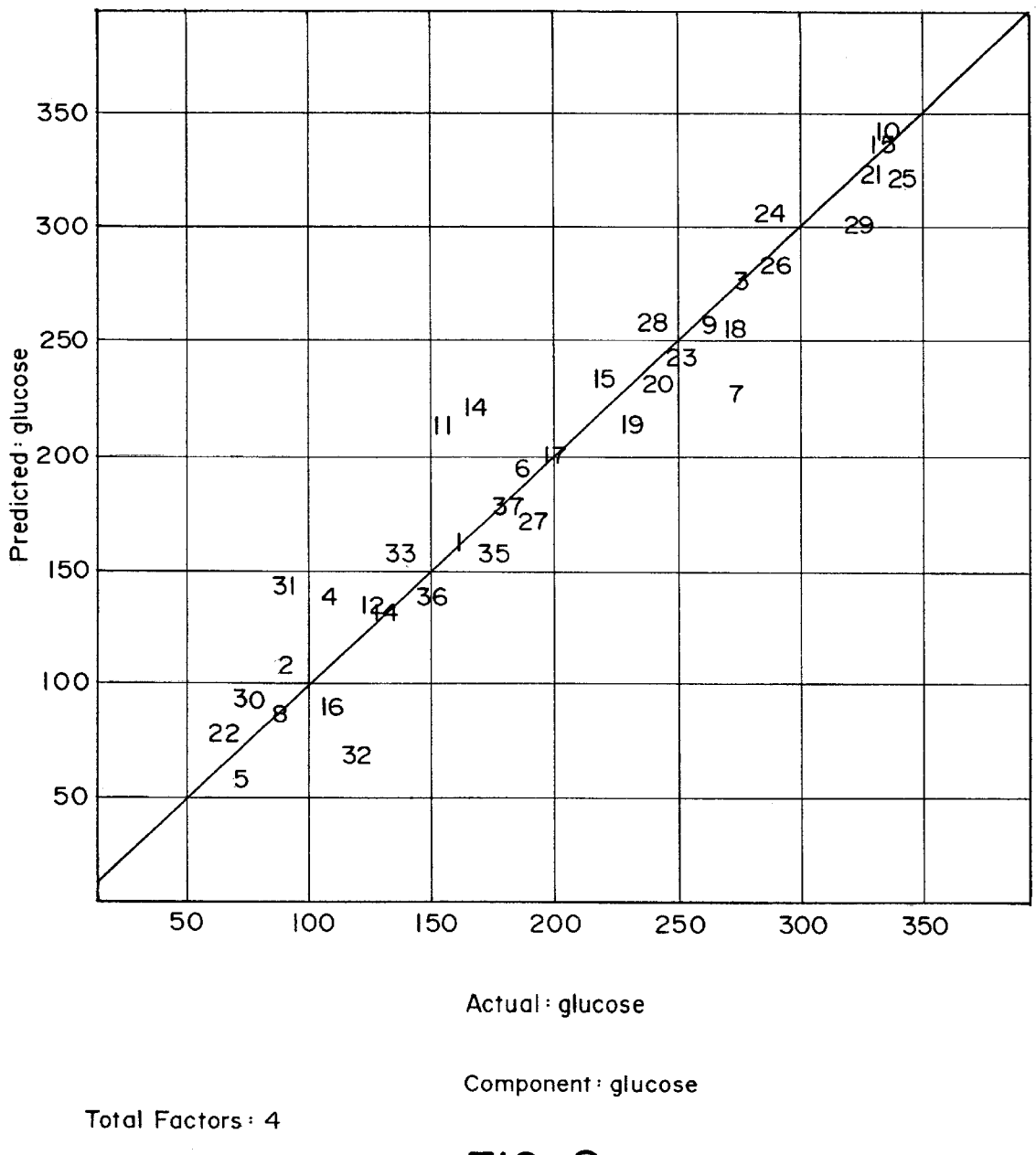
FIG. 9 is a graph of the correlation between glucose measurements made with the present invention and a calibration set of 37 plasma samples.

FIG. 9 is a correlation chart for the mid-infrared measurement of glucose concentration on an independent validation set of 37 plasma samples. The mid-infrared region of about 1185 to 960 $cm^{-1}$ was used and the validation set had a range of glucose concentrations from about 67 to 338 mg/dL. Measurements utilizing the present invention resulted in an $R^2$ of 0.930 and an RMSD of 22.1 mg/dL using the calibration equation. Note that the use of plasma samples yielded a smaller error than the error obtained when analyzing whole blood samples and a solution requiring 4 factors instead of 8 factors.

Figure 10:
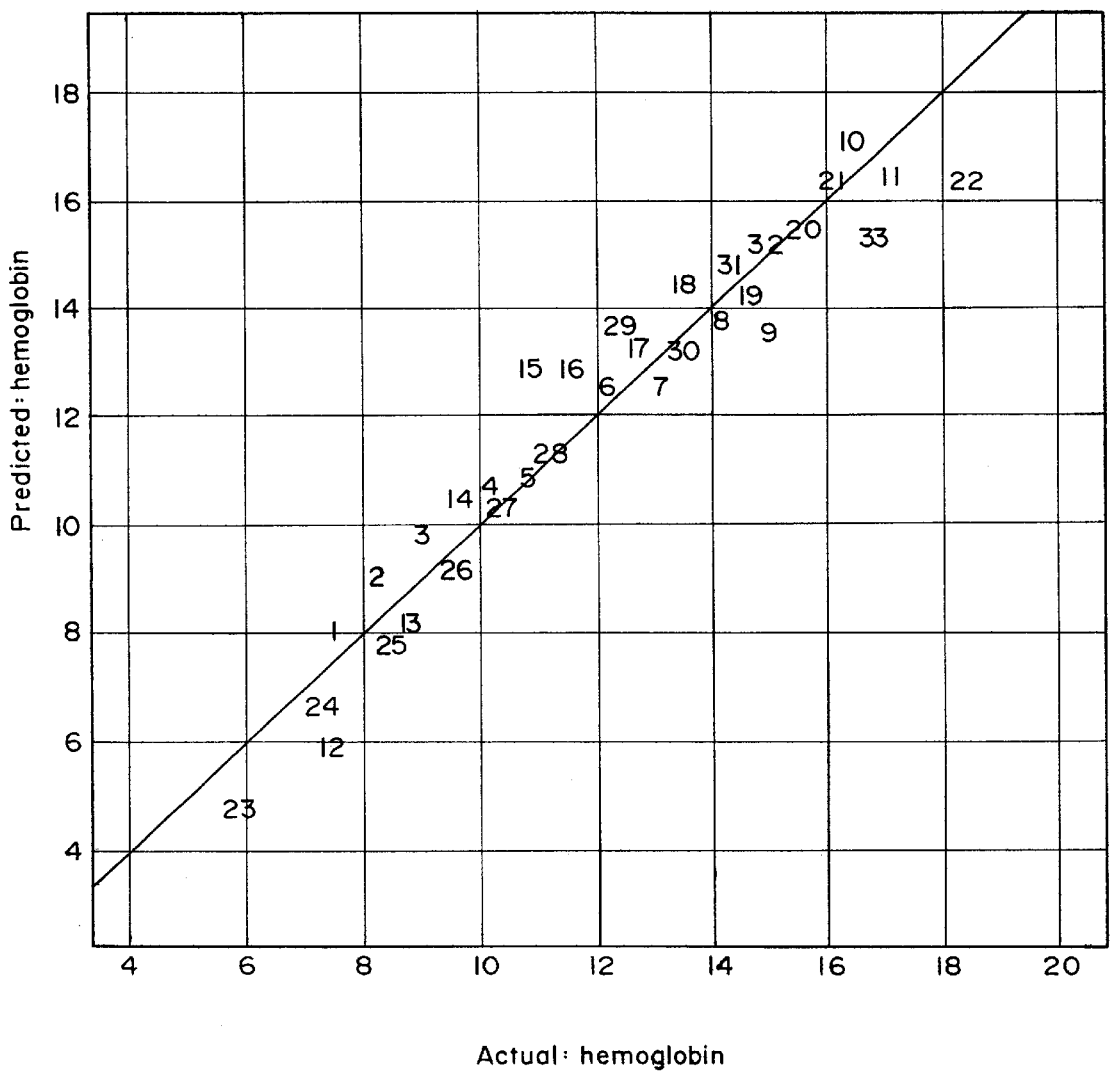
FIG. 10 is a graph of the correlation between hemoglobin measurements made with the present invention and a calibration set of 33 samples.

FIG. 10 is a correlation chart for a mid-infrared measurement of hemoglobin concentration using the region of about 1185 to 960 $cm^{-1}$ on a calibration set of 33 samples. The samples ranged in hemoglobin concentration from about 5.9 to 18.3 g/dL. Use of the present invention advantageously resulted in an $R^2$ of 0.931 and an RMSD of 0.861 g/dL.

Figure 11:
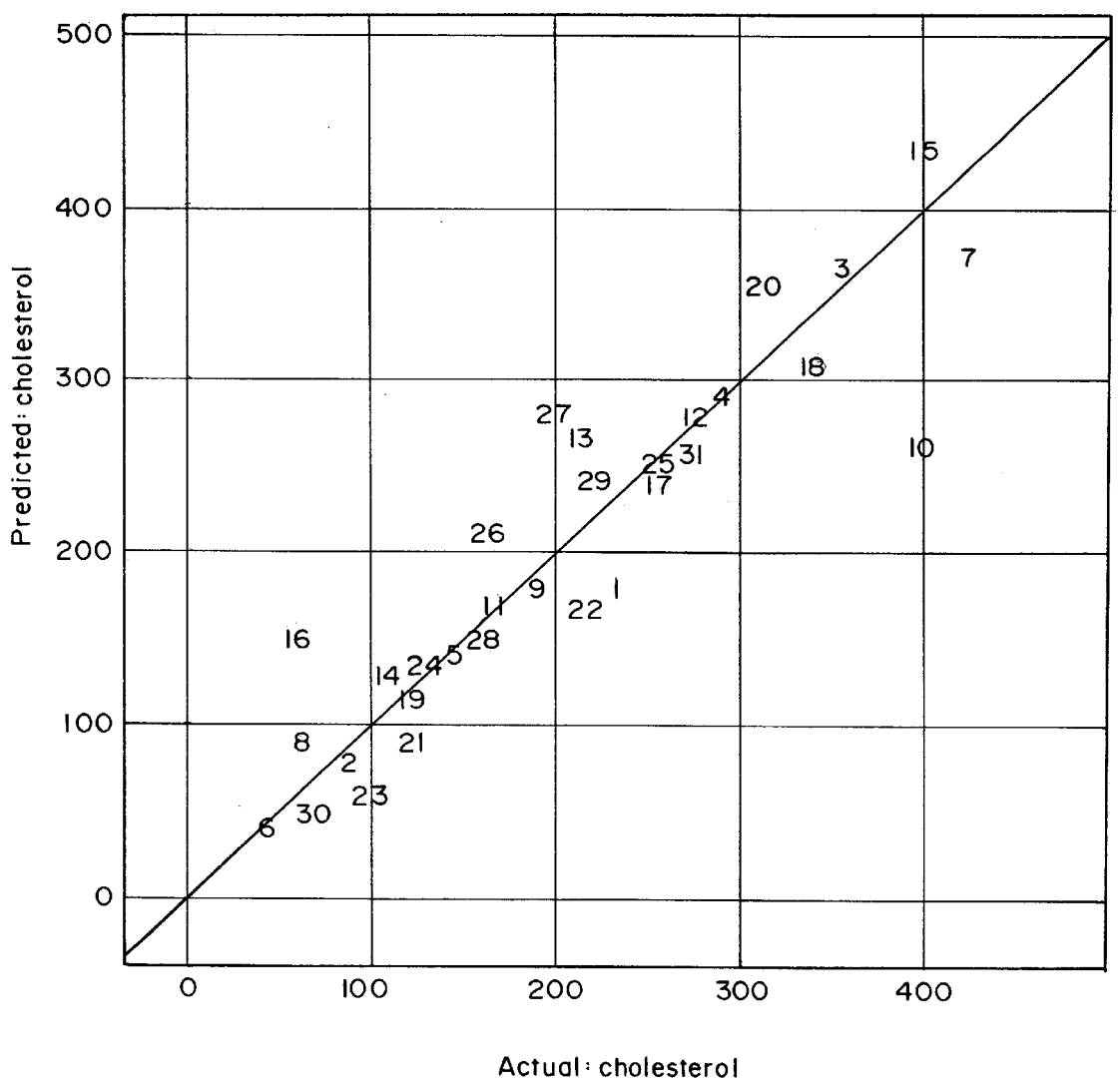
FIG. 11 is a graph of the correlation between cholesterol measurements made with the present invention and a calibration set of 31 samples.
Figure 12:
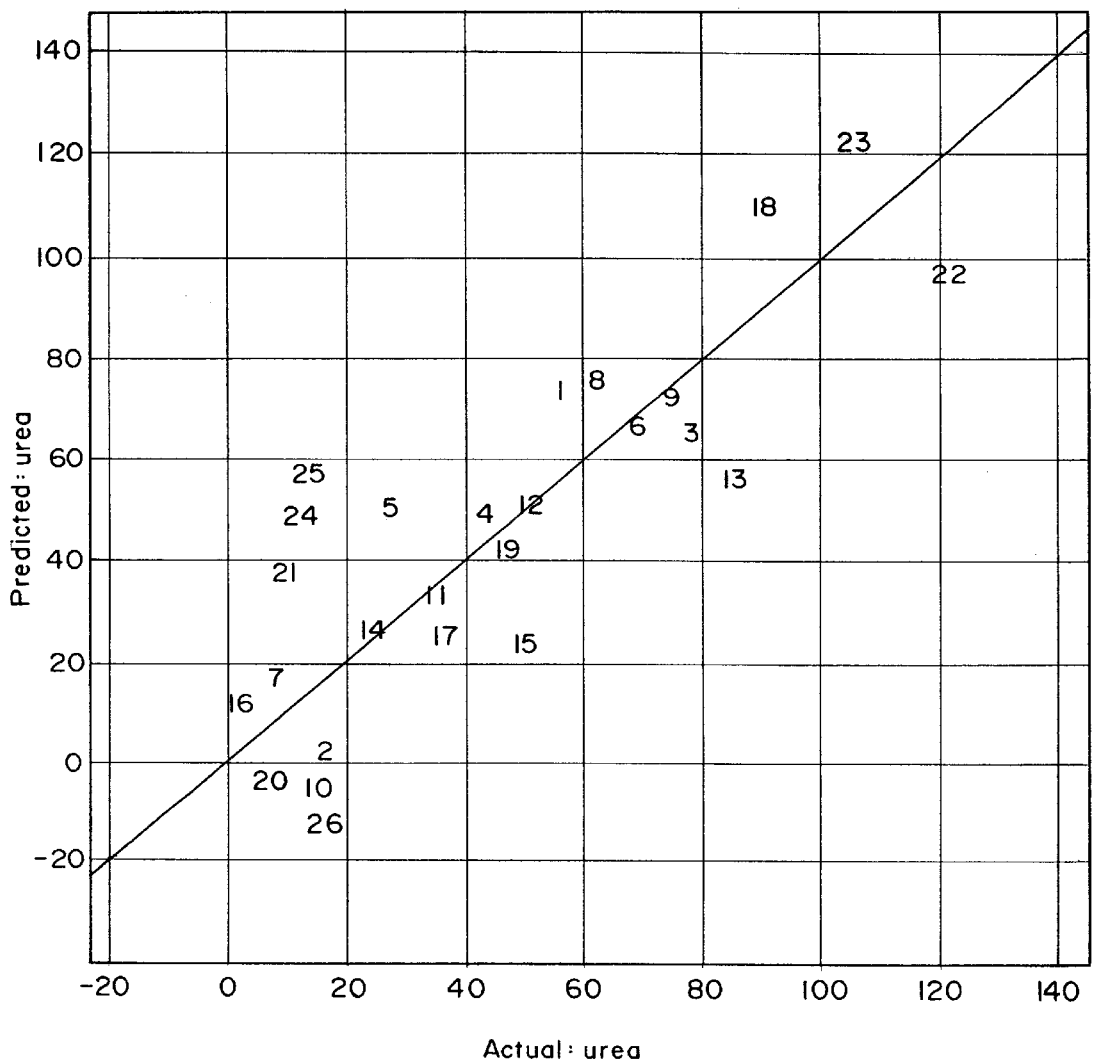
FIG. 12 is a graph of the correlation between urea measurements made with the present invention and a calibration set of 26 samples.

Similarly accurate results using the present invention were obtained for cholesterol and urea. FIG. 11 is a correlation chart for a mid-infrared measurement of cholesterol concentration using the region of about 3000 to 2800 $cm^{-1}$ on a calibration set of 31 samples. The samples ranged in cholesterol concentration from about 42 to 423 mg/dL. Use of the present invention, requiring 4 factors, resulted in an $R^2$ of 0.838 and an RMSD of 41.9 mg/dL. FIG. 12 is a correlation chart for a mid-infrared measurement of urea concentration using the region of about 1500 to 1420 $cm^{-1}$ on a calibration set of 26 samples. The samples ranged in urea concentration from 1.0 to 121.0 mg/dL. Use of the present invention, and 8 factors, resulted in an $R^2$ of 0.692 and an RMSD of 19.3 mg/dL. The lower accuracy of the results for cholesterol and urea is due to the small sample data set. Larger data set sizes would yield improved results.

Figure 13:
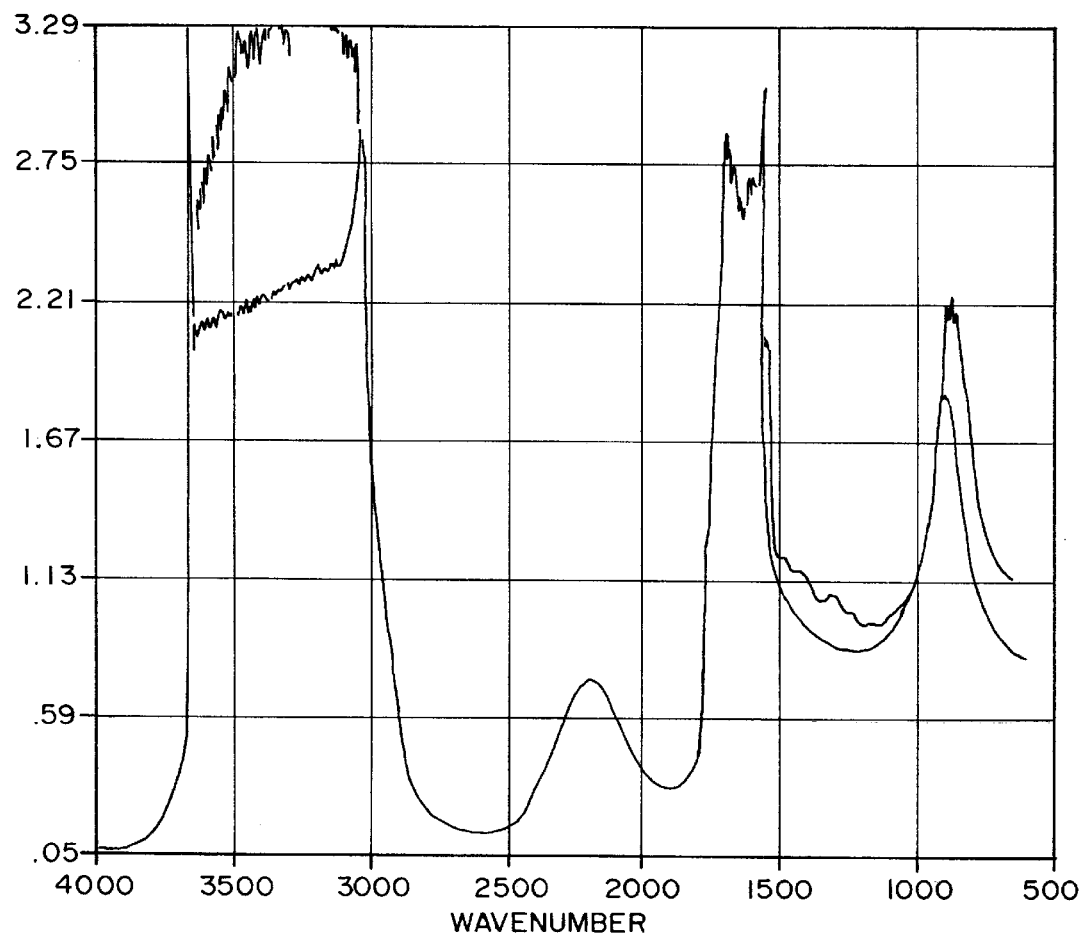
FIG. 13 illustrates the mid infrared spectrum of serum measured according to a method of the present invention.

We have found that accurate measurments may be made without precise control over the pathlength of the sample liquid film. In general, an optimal region of transmittance occurs when measurements are made in the range from an absorbance of 0.1 to 0.8, preferably 0.2 to 0.7 with the minimum occurring at an absorbance of 0.43. We believe that an improvement in measurements may be obtained by using a fixed pathlength which would yield the optimal absorbance in the desired wave number range. For serum which is similar to interstitial fluid, the optimal pathlength would be 0.007 mm. FIG. 13 illustrates the mid infrared spectrum of serum when a 0.015 mm telflon spacer was used between the barium fluoride windows. In the region from 960 $cm^{-1}$ to 1185 $cm^{-1}$, the absorbance is 0.95, which means that the absorbance would be 0.44 if the pathlength were 0.007 mm.

Figure 14:
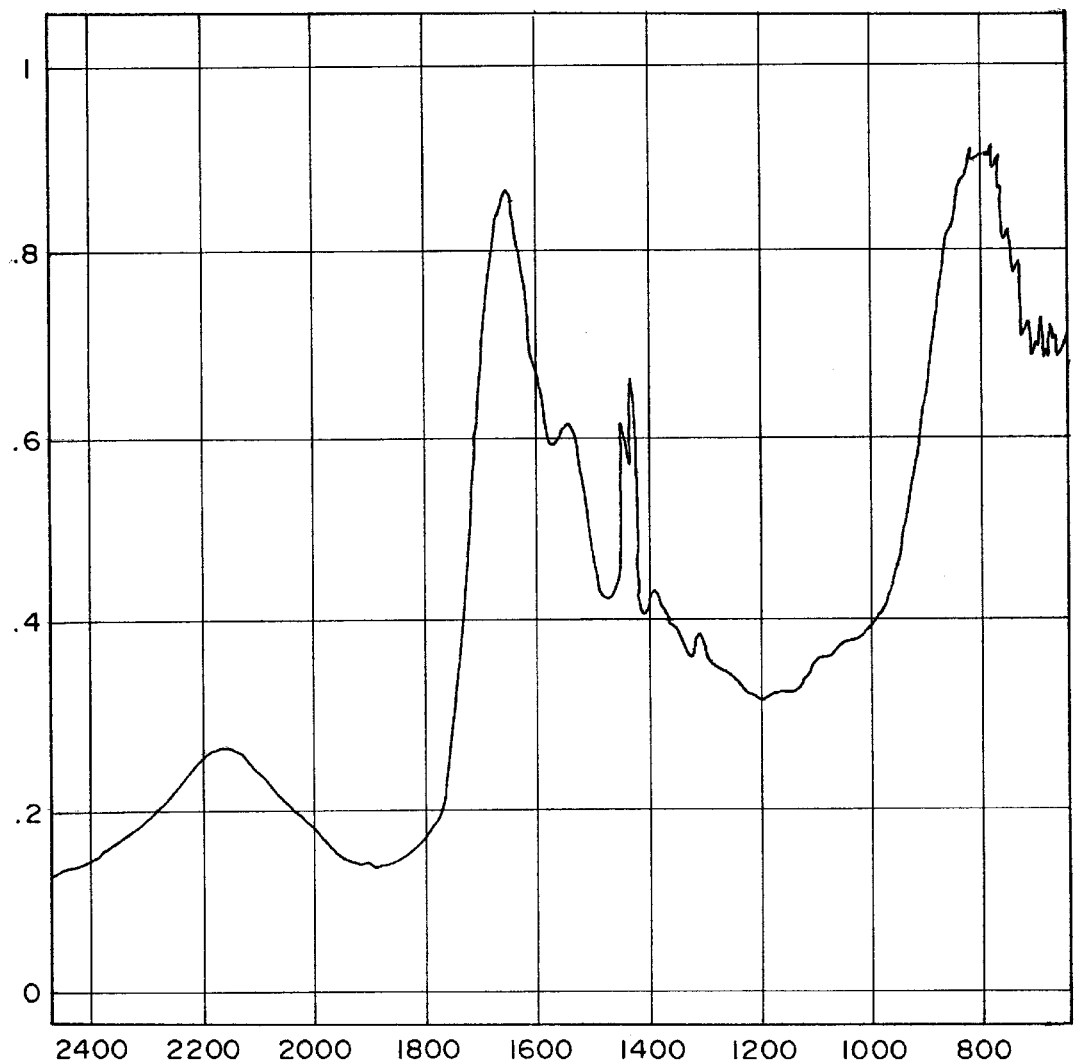
FIG. 14 is a graph of the spectrum of a plasma sample on a polyethylene card.
Figure 15:
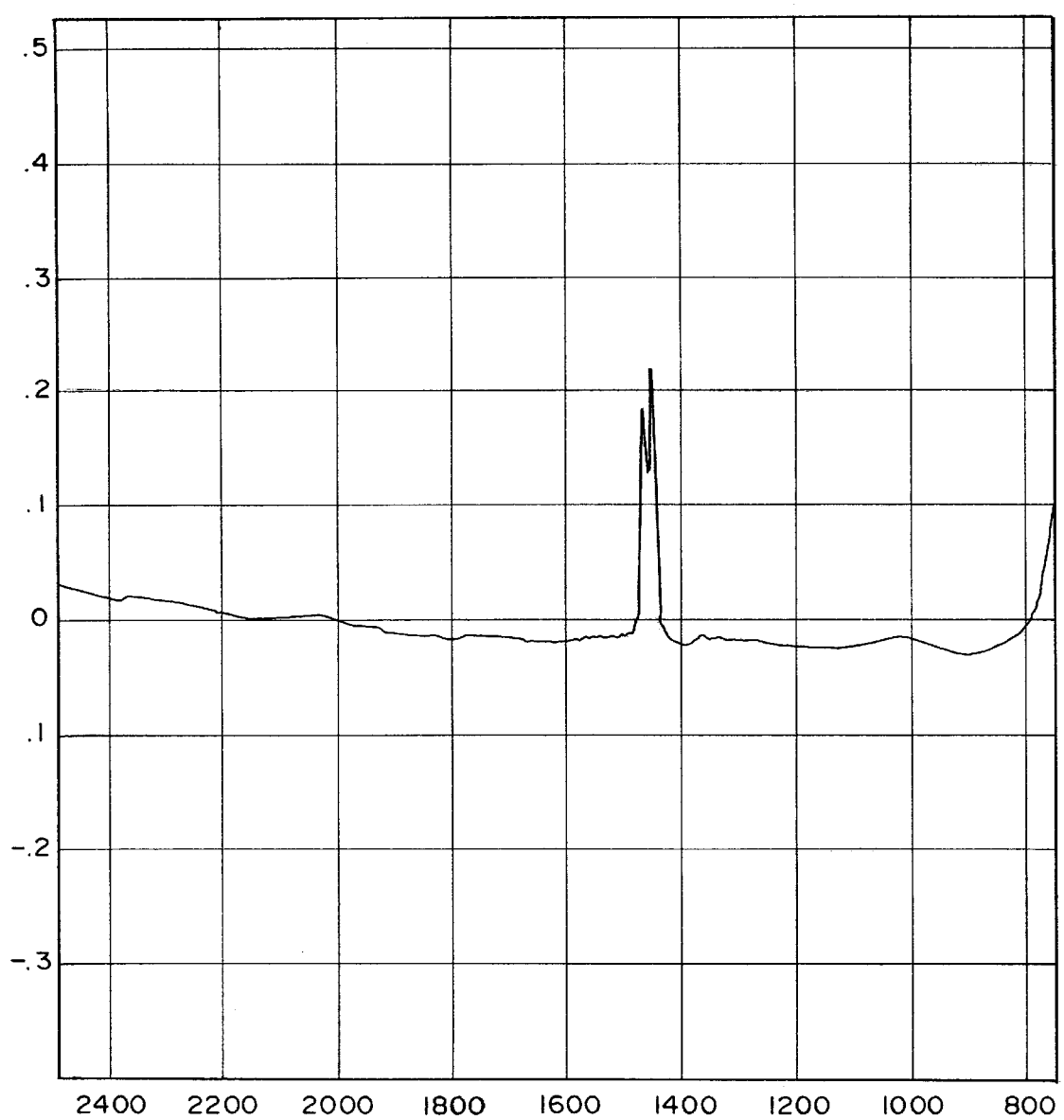
FIG. 15 is a graph of the spectrum of the polyethylene card without the plasma.

In an alternate embodiment of the present invention, the sample may be disposed on a polyethylene card a sandwiched between two barium fluoride windows (not shown). The placement of the windows allows for easier handling of the sample and further helps to prevent evaporation. FIG. 14 is the spectrum of a plasma sample that was placed on a polyethylene card and placed between barium fluoride windows to prevent evaporation. FIG. 15 is the spectrum of the polyethylene card without the plasma. Note that the polyethylene card can be used with the glucose and hemoglobin measurements described above since the only absorption band in the spectrum of polyethylene does not occur in the region of interest for glucose and hemoglobin, i.e. from about 1185 to 960 $cm^{-1}$. Conversely, the polyethylene card may interfere with the urea measurement described above. Polytetrafluoroethylene (Teflon) cards may be advantageous for the measurment of urea.

In a noninvasive setting, a method of the present invention comprises applying the analytical techniques described herein to noninvasive measurement of glucose and/or other analytes. A noninvasive method of the present invention comprises obtaining detailed spectral information, for example absorbance obtained by reflectance measurements, over a limited spectral region in which the analyte of interest has a relatively high molar absorptivity in comparision to the molar absorptivity of other substances in the path of the light beam. The spectral information may be obtained from a site on the patient's body, for example a finger tip or ear lobe, using a diode array detector. Preferably spectral information is obtained at the peak and trough of blood flow through the site, in linkage with the arterial pulse, to yield a difference spectrum (peak spectrum—trough spectrum). In order to determine analyte concentration the difference spectrum may be normalized by division by the area of the absolute value of the derivative spectrum over the limited spectral region, followed by multivariate calibration to yield data which may be correlated to the concentration of the analyte of interest. A method of the present invention may be utilized to obtain a glucose concentration measurement by performing an optical reflectance measurement on the skin surface at 960 to 1185 $cm^{-1}$ in the mid infrared or from 2035 to 2375 nm in the near infrared. A similar technique may be performed using thermal emission gradients in the mid infrared region.

Although the invention has been described with reference to these preferred embodiments, other embodiments can achieve the same results. Variations and modifications of the present invention will be apparent to one skilled in the art and the following claims are intended to cover all such modifications and equivalents.

What is claimed is:

1. An in-vitro method for determining the concentration of one or more clinical analytes comprising the steps of:
   (a) obtaining a volume of a fluid sample comprising interstitial fluid;
   (b) contacting a portion of said sample on a plane of an optically clear first window;
   (c) placing a second optically clear window in contact with the first window to thereby sandwich the sample between the windows;
   (d) shining a known wavelength of light from the mid-infrared spectrum for an uncontrolled path length through said windows and said sample in a path perpendicular to said plane;
   (e) measuring a spectrophotometric property of said light; and
   (f) performing a quantitative mathematical analysis of said spectrophotometric property to determine the concentration of at least one analyte, wherein the fluid sample is obtained by creating a micropore on the surface of the skin of a patient, wherein said micropore at least partially fills with interstitial fluid and pressing said first window against the micropore to collect a volume of said interstitial fluid.

2. The method of claim 1, wherein the step of contacting said sample on a first window further comprises the step of contacting said window with a fluid collection area.

3. An in vitro method of clinical analyte determination as recited in claim 1, wherein the step of contacting said sample on a first window further comprises the step of contacting said window whit said micropore.

4. The method of claim 1, wherein the first window comprises a barium fluoride window.

5. The method of claim 1, wherein said sample is placed on a polyethylene card sandwiched between two barium fluoride windows.

6. The method of claim 1, wherein the step of contacting said sample on a first window further comprises the step of providing a second window and opposing said second window against said sample and said first window.

7. The method of claim 1, wherein the known wavelength is in the range of about 1185 to 960 $cm^{-1}$.

8. The method of claim 1, wherein the step of performing a mathematical analysis further comprises performing a partial least squares analysis.

9. The method of claim 1, wherein the step of performing a mathematical analysis further comprises the steps of:
   (a) normalizing said spectrum; and
   (b) performing a multivariate analysis.

10. An in vitro method of clinical analyte determination as recited in claim 9, wherein the step of normalizing said spectrum further comprises dividing said spectrum by the area of the absolute value of the derivative spectrum.

11. The method of claim 1, wherein the step of performing a mathematical analysis further comprises determining the presence of glucose.

12. The method of claim 1, wherein the fluid sample comprises whole blood and the step of performing a mathematical analysis further comprises determining the presence of hemoglobin.

13. The method of claim 1, wherein the step of performing a mathematical analysis further comprising determining the presence of urea.

14. The method of claim 1, wherein the step of performing a mathematical analysis further comprising determining the presence of cholesterol.

15. The method of claim 1, wherein the step of performing a mathematical analysis further comprising determining the presence of any combination of glucose, urea and cholesterol.

16. An apparatus for clinical analyte determination, comprising:
   means for obtaining a volume of a fluid sample, wherein at least a portion of said sample is disposed on a plane of an optically clear window;
   means for shining a known wavelength of light from the mid-infrared spectrum through said window and said sample in a path perpendicular to said plane;
   means for measuring a spectrum produced by the transmittance of said light; and
   means for performing a mathematical analysis of said spectrum to determine the presence of an analyte,
   wherein the means for obtaining a volume of a fluid sample comprise means for creating a micropore on the surface of the skin of a patient that will at least partially fill with interstitial fluid and a first window for pressing against the micropore to collect a volume of said interstitial fluid.

* * * * *